United States Patent [19]
Yamasita et al.

[11] 4,113,354
[45] Sep. 12, 1978

[54] SINGLE-LENS REFLEX OPTICAL SYSTEM FOR AN ENDOSCOPE

[75] Inventors: Nobuo Yamasita, Tama; Toshihiro Imai, Hachiouji, both of Japan

[73] Assignee: Olympus Optical Co., Ltd., Japan

[21] Appl. No.: 773,408

[22] Filed: Mar. 1, 1977

[30] Foreign Application Priority Data

Mar. 3, 1976 [JP] Japan .................. 51-22080

[51] Int. Cl.$^2$ .................. G02B 27/14; G03B 19/12; A61B 1/04
[52] U.S. Cl. .................. 350/172; 350/286; 354/62; 354/152; 128/4
[58] Field of Search .................. 350/172, 173, 96 BC, 350/202, 286, 287; 354/62, 75, 76, 79, 152, 155, 156; 128/4, 6

[56] References Cited
U.S. PATENT DOCUMENTS

| 754,076 | 3/1904 | Konig | 350/286 |
| 3,918,072 | 11/1975 | Imai et al. | 350/96 BC |
| 4,021,823 | 5/1977 | Miyata | 354/155 |

FOREIGN PATENT DOCUMENTS 1,027,557  5/1953  France .................. 354/152

*Primary Examiner*—Jon W. Henry
*Attorney, Agent, or Firm*—Cushman, Darby & Cushman

[57] ABSTRACT

A single-lens reflex optical system for an endoscope comprising a first prism having a reflecting mirror with a small hole located at a position near the aperture stop of the photographing optical system, a second prism cemented to the first prism, and an observing optical system arranged near the exit surface of the second prism. In the above single-lens optical system, the aperture stop of the photographing optical system and aperture stop of the observing optical system are respectively arranged at angles close to a right angle in respect to the corresponding optical axis.

27 Claims, 4 Drawing Figures

SINGLE-LENS REFLEX OPTICAL SYSTEM FOR AN ENDOSCOPE

BACKGROUND OF THE INVENTION (a) Field of the Invention

The present invention relates to an optical system for an endoscope and, more particularly, to a single-lens reflex optical system for an endoscope.

(b) Description of the Prior Art

Most of conventional optical systems for endoscopes are of the twin-lens reflex type. That is, the observing optical system and photographing optical system are assembled in the distal end of the endoscope. Therefore, the distal end of the endoscope is necessarily long. This is not advantageous because pain of the patient who undergoes the examination becomes considerably large when such long distal end is inserted to the body cavity of the patient. To solve the above problem, a single-lens reflex optical system for an endoscope is provided as disclosed in U.S. Pat. No. 3,918,072 to Imai et al which bases priority on Japanese Patent Application No. 124,979/1972. An example of the above-mentioned single-lens reflex optical system for an endoscope is arranged as shown in FIG. 1. In FIG. 1, numeral 1 designates a cover glass, numeral 2 designates a prism, numeral 2' designates a correcting prism, numeral 3 designates a reflecting mirror having a small hole 3a at the center, numerals 4 and 5 respectively designate convex lenses, and numeral 6 designates a photographing lens. The cover glass 1, two biconvex lenses 4 and 5 and photographing lens 6 compose a photographing optical system which focuses an image on an object on a film surface 7. Numeral 8 designates a convex lens and numeral 9 designates an observing lens. Together with the cover glass 1 and convex lens 4, the convex lens 8 and observing lens 9 compose an observing optical system which focuses an image of the object on an end face 10a of an image guide 10. The afore-mentioned Japanese Patent Application also discloses another example of the single-lens reflex optical system for an endoscope which is arranged as shown in FIG. 2. The example shown in FIG. 2 differs from the example shown in FIG. 1 only in that a penta-prism 11 is used instead of the prism 2. The other details are substantially the same as those of the example shown in FIG. 1. (In FIG. 2, those members which are substantially the same as those shown in FIG. 1 are designated by the same numeral as those shown in FIG. 1.) Numeral 11' designates a correcting prism made of the glass of same quality as the penta-prism 11. Numeral 12 designates a mirror.

In cases of the above-mentioned known optical systems for endoscopes, the aperture stop of the photographing optical system and/or observing optical system is inclined in respect to the optical axes of respective optical systems. For instance, in case of the example shown in FIG. 1, the aperture stop (the small hole 3a serves as the aperture stop) of the photographing optical system is largely inclined in respect to its optical axis. In case of the example shown in FIG. 2, the aperture stop of the photographing optical system is only slightly inclined in respect to its optical axis. However, the aperture stop of the observing optical system is positioned on the surface of the mirror 12 which is formed on the penta-prism 11 and, therefore, the aperture stop is largely inclined in respect to the optical axis of the observing optical system as it is evident from FIG. 2. When the aperture stop is largely inclined in respect to the optical axis as described in the above, brightness of the focused image becomes uneven. This is because, when the aperture stop is not at a right angle to the optical axis but is inclined by an angle $\theta$ from the plane which is at a right angle to the optical axis, the aperture efficiency of the inclined aperture stop for the ray having a field angle $\alpha$ becomes as expressed by $(\cos^2(\theta \pm \alpha)/\cos^2 \theta)$. Therefore, for both of the photographing optical system and observing optical system, it is desirable that the aperture stop is positioned at an angle as far as possible close to a right angle in respect to the optical axis of the corresponding optical system.

Besides, for the photographing optical system it is possible to make the length from the lens system to the film surface shorter when the equivalent optical path of prisms constituting the photographing optical system is shorter. Therefore, for the optical systems to be used for endoscopes for which the diameter should be made as small as possible, it is desirable to make the equivalent optical path of prisms as short as possible. However, both of the above examples of known single-lens reflex optical system for an endoscope have a disadvantage that their equivalent optical paths are comparatively long.

Moreover, the distance from the entrance surface of the prism to the optical axis of lenses constituting the observing optical system and arranged between the prism and image guide should be made large. This is because the lens 1, which also serves as the cover glass, will interfere with the lens mount of the observing optical system when the above-mentioned distance is small and, consequently, it becomes difficult to arrange those members satisfactorily. To prevent such interference, in the example shown in FIG. 1, the cover glass 1 is arranged at a certain distance from the prism 2. However, this is not advantageous because the length from the cover glass to the film surface becomes large and it is contrary to the requirement to make the distal end compact. In case of the example shown in FIG. 2, the optical axis of the observing optical system is inclined toward the direction in which it goes away from the cover glass. However, this is not advantageous when manufacturing the endoscope because it is necessary to arrange the image guide in the inclined position. Besides, for single-lens reflex optical systems for endoscopes, it is preferable that the image obtained by the observing optical system becomes an erect image.

SUMMARY OF THE INVENTION

It is, therefore, a primary object of the present invention to provide a single-lens reflex optical system for an endoscope in which both of the photographing optical system and observing optical system are arranged so that the aperture stop of each optical system is positioned at an angle as close as possible to a right angle in respect to the optical axis of the corresponding optical system.

Another object of the present invention is to provide a single-lens reflex optical system for an endoscope which is arranged so that the cover glass does not interfere with the lens mount of the observing optical system and, at the same time, which is arranged compactly.

DETAILED DESCRIPTION OF THE PREFERRED EMBODIMENTS

Figure 1:
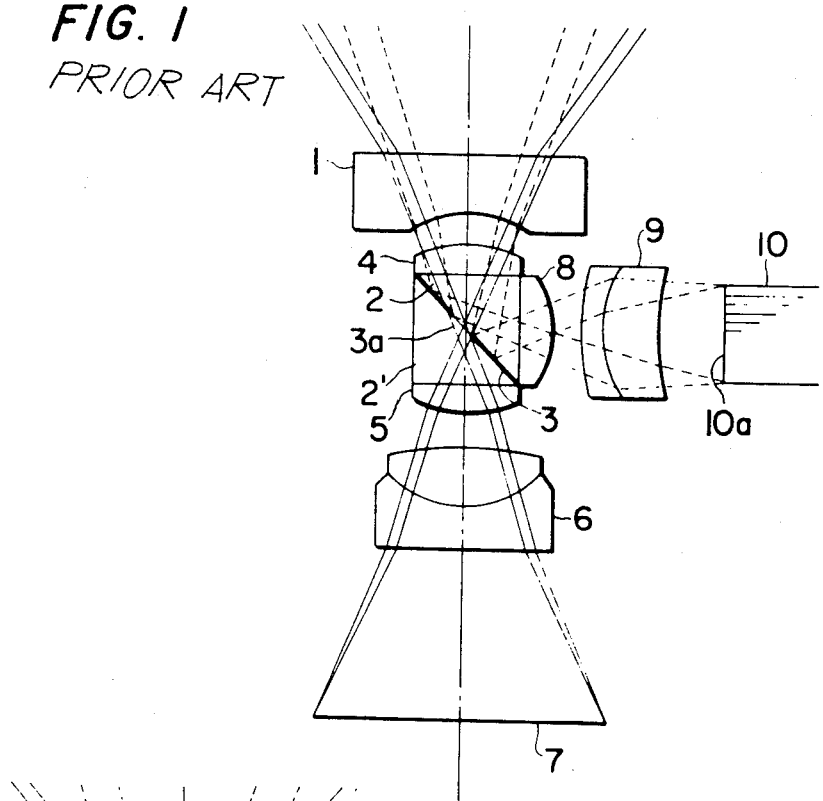
FIGS. 1 and 2 respectively show sectional views of examples of the known single-lens reflex optical system for endoscopes.
Figure 2:
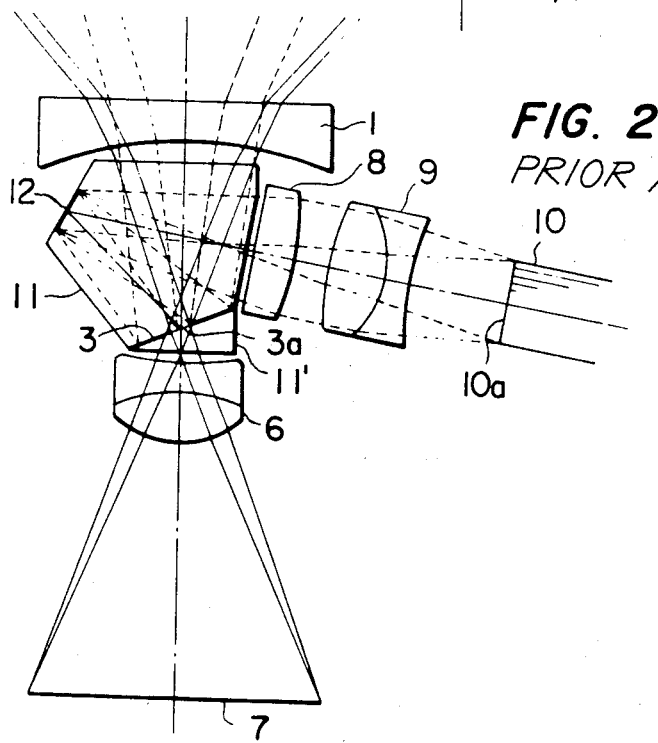
Figure 3:
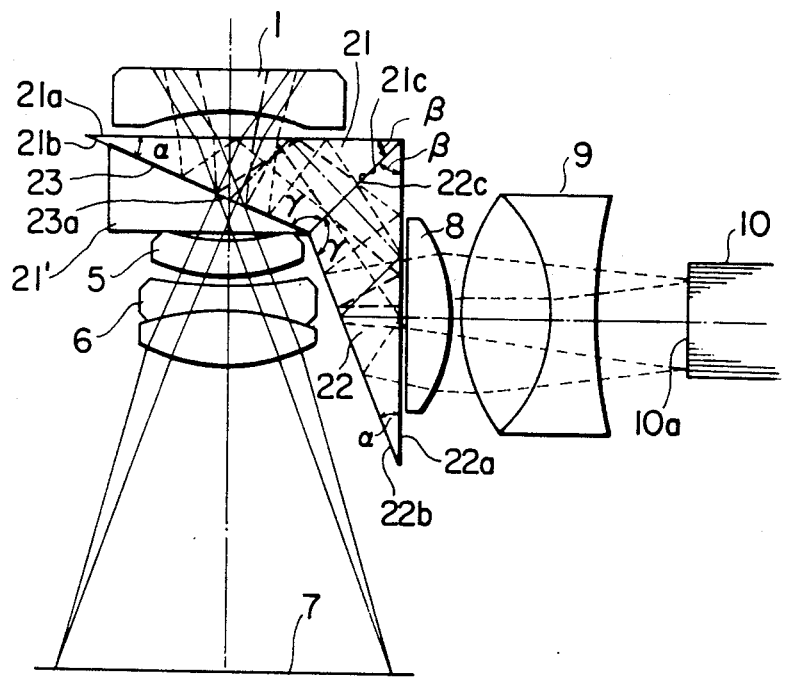
FIG. 3 shows a sectional view of a first embodiment of the single-lens reflex optical system for an endoscope according to the present invention.

In the following, the single-lens reflex optical system for an endoscope according to the present invention is described referring to the embodiments illustrated on the accompanying drawings. In FIG. 3 showing the first embodiment of the present invention, numeral 1 designates a cover glass, numerals 5 and 6 respectively designate photographing lenses, numeral 7 designates a film surface, numerals 8 and 9 respectively designate observing lenses, and numeral 10 designates an image guide. Functions of the above members are substantially the same as those of the corresponding members constituting the known examples shown in FIGS. 1 and 2. Numeral 21 designates a first triangular prism, numeral 22 designates a second prism, and numeral 23 designates a reflecting mirror formed on one surface 21b of the first prism 21 and having a small hole 23a. For the first prism 21 constituting the first embodiment, the angle α between its entrance surface 21a and surface 21b on which the reflecting mirror 23 is formed is 22.5°, the angle β between the entrance surface 21a and cemented surface 21c cemented to the second prism 22 is 45°, twice angle γ, and the angle γ between the above-mentioned cemented surface 21c and the surface 21b on which the mirror 23 is formed is 112.5° an obtuse. For the second prism 22, the angle α between its exit surface 22a and surface 22b is 22.5°, the angle β between the exit surface 22a and cemented surface 22c cemented to the first prism 21 is 45°, and the angle γ between the above-mentioned cemented surface 22c and surface 22b is 112.5°. Besides, numeral 21' designates a correcting prism.

In the single-lens reflex optical system for an endoscope arranged as described in the above, the light from the object to be observed passed through the cover glass 1 and small hole 23a are focused on the film surface 7 by means of photographing lenses 5 and 6 so that the object is photographed onto the film surface 7. On the other hand, a part of the light from the object is reflected by the reflecting mirror 23 and is then totally reflected by the surface 21a of the first prism 21. After that, said light enters the second prism through the cemented surface between the first prism 21 and second prism 22, goes out of the second prism 22, and is focused on the end face 10a of the image guide 10 by means of the observing lenses 8 and 9. After that, said light is transmitted by the image guide 10 to the other end thereof so that the object is observed.

In the above-mentioned single-lens reflex optical system, the aperture stop for the photographing optical system exists at the position of the small hole 23a while the aperture stop of the observing optical system exists on the cemented surface between the first prism 21 and second prism 22. Therefore, as it is evident from FIG. 3, the surface on which the aperture stop of the photographing optical system exists (the surface of the reflecting mirror 23) is positioned at a large angle from the optical axis of the photographing optical system and said angle is comparatively close to 90°. Besides, the surface on which the aperture stop of the observing optical system exists (the cemented surface) is positioned at 90° from the optical axis of the observing optical system. In other words, for both of the photographing optical system and observing optical system, the angle between the aperture stop and optical axis of the corresponding optical system is larger than the corresponding angle of known examples. Moreover, the equivalent optical path in the photographing optical system is extremely short, the distance from the entrance surface of the prism, i.e., from the surface 21a of the first prism 21, to the optical axis of the observing optical system is large, and the image obtained by the observing optical system is an erect image.

For this embodiment, angles α, β, and γ of respective prisms are not limited to the afore-mentioned values. When, however, the angle α becomes considerably larger than 22.5°, the angle between the surface on which the aperture stop of the photographing optical system exists and optical axis of the photographing optical system will become considerably smaller than 90° and this is not desirable for attaining the object of the present invention. On the other hand, when the angle α becomes considerably smaller than 22.5°, the prisms will become very large. Moreover, it will become impossible to attain total reflection on the surface 21a etc. for the light to be transmitted by the observing optical system.

Figure 4:
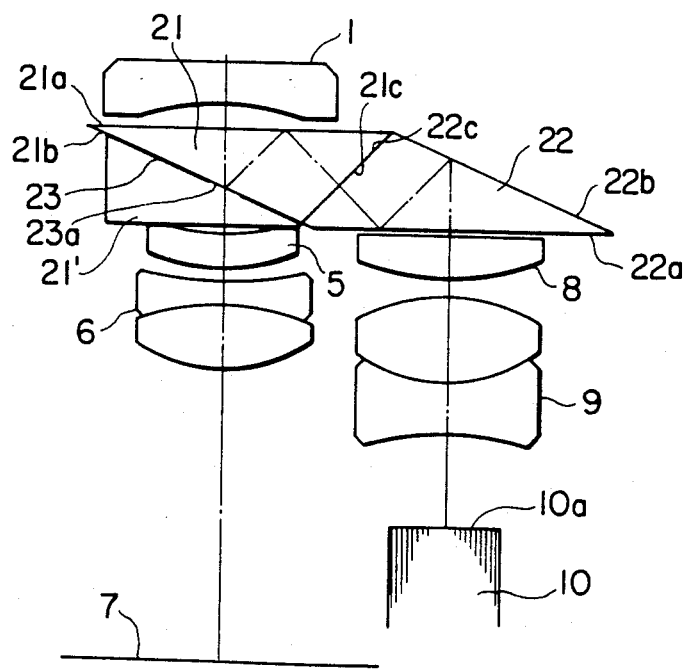
FIG. 4 shows a sectional view of a second embodiment of the present invention.

Now, FIG. 4 shows the second embodiment of the single-lens reflex optical system according to the present invention.

The second embodiment differs from the first embodiment in that the position of the second prism 22 in relation to the first prism 21 is different from that of the first embodiment. That is, in the first embodiment, the second prism 22 is arranged so that the exit surface 22a thereof is positioned approximately at a right angle to the entrance surface 21a of the first prism 21. On the other hand, in the second embodiment, the second prism 22 is arranged so that the exit surface 22a thereof becomes approximately parallel with the entrance surface 21a of the first prism 21. Therefore, as it is evident from the figures, the second embodiment is for forward viewing while the first embodiment is for side viewing.

As explained in the above, for the single-lens reflex optical system according to the present invention, each of the photographing optical system and observing optical system has the aperture stop positioned at 90° or at an angle close to 90° in respect to the corresponding optical axis. Therefore, it is possible to obtain a favourable image, for which brightness is even, for both photographing and observing. Moreover, as the equivalent optical path of prisms arranged in the optical system is short, it is possible to make the diameter of the endoscope small. Besides, as the distance from the entrance surface of the prism to the optical axis of the observing optical system is large, it is possible to easily arrange so that the cover glass and lens mount of the observing lenses will not interfere with each other.

We claim:

1. A single-lens reflex optical system for an endoscope comprising:
   a photographing optical system for focusing an image of an object to be observed on a film surface;
   a first prism having an entrance surface and a mirrored surface for reflecting object light received through said entrance surface by, sequentially, said mirrored surface and said entrance surface of said first prism;
   said mirrored surface having a small hole arranged close to the position of the aperture stop of said photographing optical system for permitting a portion of said object light to pass to said film surface;

a second prism centered to said first prism and having a reflecting surface and an exit surface for receiving object light reflected by said entrance surface of said first prism and for reflecting said received object light by, sequentially, said exit surface and said reflecting surface of said second prism before said received object light passes out of said second prism through said exit surface;

a correcting prism cemented to said mirrored surface of said first prism;

an image guide having an end face; and an observing optical system disposed near said exit surface of said second prism for focusing the object light passing out of said exit surface of said second prism into said image guide face.

2. A single-lens reflex optical system for an endoscope according to claim 1, in which said first and second prisms are arranged so that said entrance surface of said first prism is positioned approximately at a right angle to said exit surface of said second prism.

3. A single-lens reflex optical system for an endoscope according to claim 1, in which said first and second prisms are arranged so that said entrance surface of said first prism is positioned approximately in parallel with said exit surface of said second prism.

4. A single-lens reflex optical system for an endoscope according to claim 1 wherein said first prism is arranged so that the angle between said entrance surface and said mirrored surface is in the area of 22.5°.

5. A single-lens reflex optical system for an endoscope according to claim 1 wherein said first prism is triangular and said first prism is arranged so that the angle between said mirrored surface and the cemented surface cemented to said second prism is obtuse.

6. A single-lens reflex optical system for an endoscope according to claim 5 wherein the mangitude of the angle between said entrance surface and said cemented surface is twice the magnitude of the angle between said entrance surface and said mirrored surface.

7. A single-lens reflex optical system for an endoscope according to claim 5 wherein the angle between said entrance surface and said cemented surface is in the area of 45°.

8. A single-lens reflex optical system for an endoscope according to claim 6 wherein the angle between said entrance surface and said cemented surface is in the area of 45°.

9. A single-lens reflex optical system for an endoscope according to claim 5 wherein said first prism is arranged so that the angle between said mirrored surface and said cemented surface is in the area of five times the magnitude of the angle between said entrance surface and said mirrored surface.

10. A single-lens reflex optical system for an endoscope according to claim 5 wherein said first prism is arranged so that the angle between said entrance surface and said mirrored surface is in the area of 22.5°.

11. A single-lens reflex optical system for an endoscope according to claim 1 wherein the brightness of the image on both said film surface and said end face of said image guide is substantially even.

12. A single-lens reflex optical system for an endoscope according to claim 1, in which said first prism is arranged so that the angle between said entrance surface and said mirrored surface is in the area of 22.5°, the angle between said entrance surface and the cemented surface cemented to said second prism is in the area of 45°, and the angle between said cemented surface and said mirrored surface is in the area of 112.5°.

13. In combination:

an endoscope having a distal end containing a single-lens reflex optical system for evening the brightness of an object image focused onto a film surface, said optical system comprising:

a photographing optical system for focusing said image on said film surface;

a first prism having an entrance surface and at an acute angle therefrom a mirrored surface for reflecting object light received through said entrance surface by, sequentially, said mirrored surface and said entrance surface of said first prism;

said mirrored surface having a small hole arranged close to the position of the aperture stop of said photographing optical system for permitting a portion of said object light to pass to said film surface;

a second prism cemented to said first prism and having a reflecting surface and an exit surface for receiving object light reflected by said entrance surface of said first prism and for reflecting said received object light by, sequentially, said exit surface and said reflecting surface of said second prism before said received object light passes out of said second prism through said exit surface;

an image guide having an end face; and an observing optical system disposed near said exit surface of said second prism for focusing the object light passing out of said exit surface of said second prism onto said image guide face.

14. Apparatus as in claim 13 wherein said first prism entrance surface is substantially perpendicular to said second prism exit surface.

15. Apparatus as in claim 13 wherein the axis of said object light entering said first prism is perpendicular to the axis of said object light focused on said image guide end face.

16. Apparatus as in claim 13 wherein said first prism entrance surface is substantially parallel to said second prism exit surface.

17. Apparatus as in claim 13 wherein the axes of said object light entering said first prism and focused on said image guide end face are parallel.

18. Apparatus as in claim 13 wherein said first prism is arranged so that the angle between said entrance surface and said mirrored surface is in the area of 22.5°.

19. Apparatus as in claim 13 wherein said first prism is triangular and said first prism is arranged so that the angle between said mirrored surface and the cemented surface cemented to said second prism is obtuse.

20. Apparatus as in claim 19 wherein the magnitude of the angle between said entrance surface and said cemented surface is twice the magnitude of the angle between said entrance surface and said mirrored surface.

21. Apparatus as in claim 19 wherein the angle between said entrance surface and said cemented surface is in the area of 45°.

22. Apparatus as in claim 20 wherein the angle between said entrance surface and said cemented surface is in the area of 45°.

23. Apparatus as in claim 19 wherein said first prism is arranged so that the angle between said mirrored surface and said cemented surface is in the area of five times the magnitude of the angle between said entrance surface and said mirrored surface.

24. Apparatus as in claim 19 wherein said first prism is arranged so that the angle between said entrance surface and said mirrored surface is in the area of 22.5°.

25. Apparatus as in claim 13 wherein the brightness of the image on both said film surface and said end face of said image guide is substantially even.

26. Apparatus as in claim 13, in which said first prism is arranged so that the angle between said entrance surface and said mirrored surface is in the area of 22.5°, the angle between said entrance surface and the cemented surface cemented to said second prism is in the area of 45°, and the angle between said cemented surface and said mirrored surface is in the area of 112.5°.

27. A single-lens reflex optical system for an endoscope comprising:

a photographing optical system for focusing an image of an object to be observed on a film surface;

a first prism having an entrance surface, a mirrored surface, and a cemented surface, said first prism being arranged so that the angle between said entrance surface and said mirrored surface is 22.5°, the angle between said entrance surface and said cemented surface is 45°, and the angle between said cemented surface and said mirrored surface is 112.5°;

said mirrored surface having a small hole arranged close to the position of the aperture stop of said photographing optical system;

a second prism cemented to said cemented surface of said first prism and having a reflecting surface and an exit surface;

an observing optical system disposed near said exit surface of said second prism; and an image guide;

said single-lens reflects optical system for an endoscope being arranged so that the light from said object reflected by said mirrored surface is further reflected by said entrance surface of said first prism, enters said second prism, is reflected respectively by said exit surface and said reflecting surface of said second prism, before passing out through said exit surface of said second prism and being focused on an end face of said image guide by said observing optical system.

* * * * *